United States Patent [19]

Okubo

[11] Patent Number: 4,707,238
[45] Date of Patent: Nov. 17, 1987

[54] METHOD OF PROCESSING A METAL SURFACE

[76] Inventor: Tadanobu Okubo, No. 400-240, Kamiza, Sakura-shi, Chiba-ken, Japan

[21] Appl. No.: 863,682

[22] Filed: May 15, 1986

[51] Int. Cl.$^4$ ............................................. C23C 14/00
[52] U.S. Cl. ..................... 204/192.31; 204/192.38; 427/38
[58] Field of Search ........... 204/192 R, 192 C, 192 N, 204/192.31, 192.38, 192.1; 427/38

[56] References Cited

U.S. PATENT DOCUMENTS

| | | | |
|---|---|---|---|
| 4,197,175 | 4/1980 | Moll et al. | 204/192 N X |
| 4,226,082 | 10/1980 | Nishida | 204/192 N X |
| 4,226,932 | 10/1980 | Ferraris . | |
| 4,415,421 | 11/1983 | Sasanuma | 204/192 N |
| 4,419,202 | 12/1983 | Gibson | 204/192 N |
| 4,461,799 | 7/1984 | Gavrilov et al. | 204/192 N X |
| 4,468,309 | 8/1984 | White . | |
| 4,591,418 | 5/1986 | Snyder | 204/192 N X |

Primary Examiner—John F. Niebling
Assistant Examiner—Nam X. Nguyen
Attorney, Agent, or Firm—Young & Thompson

[57] ABSTRACT

A primary thin hard coating selected from chrome nitride, titanium nitride and titanium carbide, and a secondary thin coating selected from elemental metals and their corresponding alloys capable of dry-plating are provided on a metal material by an ion-plating technique. The secondary thin coating is provided by ion-plating in the absence of an inert gas, such as argon or helium, which is different from conventional methods for ion-plating the elemental metal in the presence of such inert gas.

4 Claims, 4 Drawing Figures

METHOD OF PROCESSING A METAL SURFACE

FIELD OF THE INVENTION

This invention relates to a method of processing a metal surface, particularly in which a metal material is coated with a primary thin film of hard metal compound and further thereon with a secondary thin film of an elemental metal or an alloy by use of an ion-plating technique to form a beautiful and glossy metal surface of high durability on a whole surface of the metal material or in a desired pattern.

BACKGROUND OF THE INVENTION

There have been known a number of articles, such as a wrist watch, cuffs, an eye-glass frame, a tie-pin, a brooch, a stationery and other accessories or outer decorations, as well as a cap crown for a tooth or dental prosthetic in which a metal material is plated with a noble metal, such as gold. There have also been well-known in the art several methods for the purpose. These conventional articles, however, have a disadvantage in that the noble metal coating tends to come off and form specks in areas of frequent use, which adversely affect durability and appearance of the articles. Further, metal articles having on their surfaces lustrous patterns are also commercially available, which are, however, poor in durability and tend to come off by rubbing.

In order to overcome those disadvantages, there has been proposed an ion-plating method for forming a primary thin coating of hard metal compound on a surface of a metal material followed by a further ion-plating procedure for forming a secondary thin film of an elemental noble metal or an alloy having a similar color tone to that of the primary coating (GB Pat. No. 2000812A). The applicant has also developed a method of forming primary and secondary films over a whole area of a metal material or in a desired pattern, similarly an utilizing the ion-plating technique (UK Patent Application No. 8518159).

In general, a film-forming method utilizing the ion-plating technique comprises ionization of a portion of vaporized metal particles followed by deposition thereof on a solid surface to form a film, in which the ionization in the presence of an inert gas (such as argon or helium) provides a film of pure metal (elemental metal), whereas the ionization in the presence of an active gas (such as oxygen or nitrogen) provides a hard film of metal oxides or nitrides. Such procedure has been generally known as a conventional method for ion-plating in the art (Scientific Dictionary, Maruzen Co., Ltd., Page 53 (1985)).

GB Pat. No. 20000812A has also utilized the conventional method, as described in Examples, in which a primary film is formed in the presence of nitrogen as the active gas while a secondary film is formed in the presence of argon as the inert gas.

It has now been found out as a result of continued study of forming the two layered coatings of primary and secondary films by means of the ion-plating technique that the ion-plating procedure in the absence of the inert gas (such as argon or helium) during formation of the secondary film of elemental metal or its alloy differently from the conventional method may avoid operation, such as a high frequency output of argon gas pressure, and improve its operability. Further, a spattering phenomenon with an argon ion may be eliminated to increase a rate of forming a thickness of the film and to lower a treatment temperature, so that the material may be prevented from damage. In the absence of the inert gas (such as argon or helium), it has also been found out that the ionization may occur only with an evaporated metal to enable vacuum in an apparatus to be reduced to $10^6$–$10^5$ Torr which is lower by $10^2$–$10^3$ Torr than the order of $10^8$ Torr in the conventional method, to increase purity of the resulting film due to the absence of inclusion of, for example, the argon ion and to prevent pin holes, resulting in improvement of corrosion-resistance. Further, the enhanced ionization of the evaporated metal permits working in a place of lower voltage applied to a cathode, thereby to reduce troubles due to abnormal discharge.

Accordingly, an object of the invention is to provide a method of processing a metal surface by means of an ionplating technique, which is superior in operability, economy and properties of products to conventional ion-plating methods when a hard primary metal film is formed on a surface of a metal material followed by a secondary film of elemental metal or its alloy thereon.

SUMMARY OF THE INVENTION

In order to achieve the object, the method according to the invention is characterized in that a metal material is subjected to bombard treatment in the presence of an inert gas followed by a first ion-plating procedure in the presence of an active gas to form on a surface of said metal material a primary thin coating of hard metal compound selected from chrome nitride, titanium nitride and titanium carbide, and that the resulting metal material with the primary thin coating is then subjected to a second ionplating procedure in the absence of an inert gas to form on said primary thin coating a secondary thin coating of an elemental metal or an alloy capable of dry-plating.

As the inert gas used for forming the primary film, there may be preferably mentioned argon and helium, especially argon, while nitrogen is preferred for the active gas. During formation of the secondary film, neither of these inert and active gases are not used, of course, As the elemental metal for the secondary film, there may be mentioned metal capable of dry-plating, such as gold, silver, platinum, copper, zinc, palladium, chrome, rhodium, indium, nickel, germanium, cobalt, zirconium, tungsten, tantalum, niobium, manganese, molybdenum, tin, iron or aluminium.

As the alloy for the secondary film, there may be mentioned an alloy capable of dry-plating selected from alloys of gold, silver, platinum, copper, palladium, chrome, rhodium, indium, nickel, germanium, cobalt, zirconium, tungsten, tantalum, niobium, manganese, molybdenum, tin, iron, zinc and aluminium.

The primary and/or the secondary films may be formed over a whole surface of the metal material or in a desired pattern. The latter case is suitable for providing a brand name or an initial on an outer accessory.

In accordance with the invention, the secondary metal film is formed on the primary hard metal film in the absence of the inert gas (such as argon), so that operation such as a high frequency output of argon gas pressure may be avoided to improve its operability, that a spattering phenomenon with an argon ion may be eliminated to increase a rate of forming a thickness of the film and to lower a treatment temperature, and that the ionization may occur only with an evaporated metal to enable vacuum in an apparatus to be reduced upto $10^6$–$10^5$ Torr which is lower by $10^2$–$10^3$ Torr than the order of $10^8$ Torr in the conventional method, to increase purity of the resulting film due to the absence of inclusion of the argon ion and to prevent pin holes, resulting in improvement of corrosion-resistance. Further, the enhanced ionization of the evaporated metal permits working in a place of lower voltage applied to a cathode, thereby to reduce troubles due to abnormal discharge.

The invention will now be described hereinbelow for its preferred embodiments with reference to the accompanying drawings.

PREFERRED EMBODIMENTS OF THE INVENTION

Figure 1:
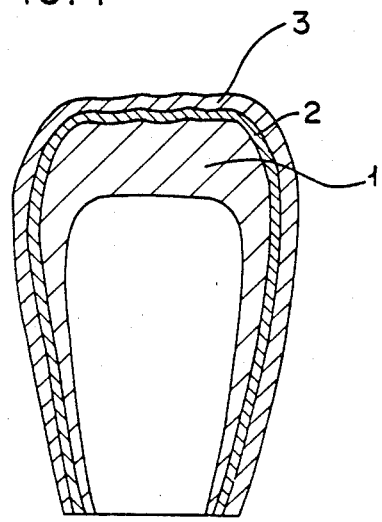
FIG. 1 is a sectional view of a finished product prepared by the method according to the invention.

In FIG. 1, reference numeral 1 represents a cap crown formed of a zinc alloy, for example, as a metal material and applied on a cured tooth. A surface of the crown 1 is coated with a prime coating 2 of titanium nitride as a hard metal compound in a thickness of $3\mu$ by means of an ionplating procedure.

Thus, the surface of the crown 1 is coated with the prime coating of golden color, which has a surface hardness of 1720 HD and a high corrosion-resistance. The golden color, however, is somewhat inferior to that of genuine gold.

Then, a surface of the prime thin coating 2 is coated with a secondary thin coating 3 of metal gold in a thickness of 5–10$\mu$. In order to form the secondary coating 3, the ion- plating procedure is essentially carried out in the absence of an inert gas, such as an argon or helium gas.

Figure 2:
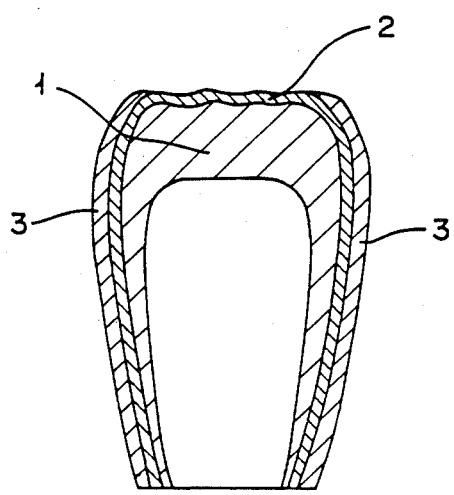
FIG. 2 is a sectional view of the product after use for some period of time.

The crown 1 thus processed has the secondary thin coating 3 of gold, which shows the true gold color. However, the gold as the secondary coating 3 is very soft and weak, so that frequent use of the crowned tooth may wear off the coating 3, as shown in FIG. 2. Under the secondary coating 3, however, there exists the prime coating 2 of titanium nitride, which shows a golden color similar to the true gold, thereby to prevent specks from occurring after wearing off the secondary coating 3. Usually, the cap crown 1 of such type is used for a back tooth, so that the apparant golden color may be kept for a long period of use.

Figure 3:
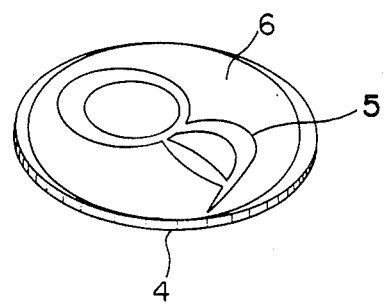
FIG. 3 is a perspective view of another product with a patterned coating.

As shown in FIG. 3, at first a whole surface of an accessory material 4, such as a tie-pin, cuffs or a brooch, may be coated with a thin coating 5 of black titanium carbide by the ion-plating procedure under the same condition as in the crown 1. Then, the tin coating 5 of titanium carbide is masked with a suitable pattern or a name, on which is coated a secondary thin coating 6 of platinum by the ion-plating procedure in the absence of the inert gas, such as argon. Thereafter, the masking is removed to leave the pattern coating.

The prime coating 5 of titanium carbide has a very high hardness to be protected from damage, while the coating 6 of platinum is also protective from damage, so that a durable and luxurious accessory may be obtained.

Further, the surface of the metal material may be coated with a thin coating of chrome nitride by the ion-plating procedure, which is then subjected to a further coating of silver alloy by the ion-plating technique in the absence of the inert gas to form a durable and luxurious product which is prevented from occurrence of specks, as in the coating in combination of titanium nitride and gold.

Similarly, the prime thin coating 5 of the hard metal compound, such as chrome nitride, titanium nitride or titanium carbide, which has been coated on the metal material by the ion-plating procedure, may be coated also by the ion-plating procedure in the absence of the inert gas with a secondary thin coating 6 of an elemental metal or an alloy capable or dry-plating selected from gold, silver, platinum, copper, zinc, palladium, chrome, rhodium, indium, nickel, germanium, cobalt, zirconium, tungsten, tantalum, niobium, manganese, molybdenum, tin and iron, as well as their corresponding alloys, to form durable and beautiful products having lustrous patterns of metal or noble metal.

In accordance with the invention, the surface of the metal material may be coated by the ion-plating technique with the prime thin coating of hard metal compound, such as chrome nitride, titanium nitride or titanium carbide, which may be then subjected to a further coating process of an elemental metal or an alloy capable of dry-plating, such as copper or its alloy by the ion-plating procedure in the absence of the inert gas, which is further plated with a suitable metal by a dry- or wet-plating method. Thus, the difficulty of the dry- or wet-plating for the titanium nitride coating may be eliminated by intervening the secondary metal coating through the ion-plating procedure in the absence of the inert gas. In this case, a similarly durable and beautiful coating may be obtained as in the previous embodiments.

In accordance with the invention, the surface of the metal material may be readily made durable and lustrous at a low cost by ion-plating combination of the hard prime coating with the secondary coating of elemental metal or alloy over its whole area or in a desired pattern.

Namely, the surface of the metal material is coated by the ion-plating procedure with the prime thin coating of the hard metal compound, such as chrome nitride, titanium nitride or titanium carbide, which prime coating is further coated by the ion-plating technique in the absence of the inert gas (such as argon or helium) with the secondary coating of elemental metal or alloy, as described hereinabove, over its whole area or in a desired pattern, so that the wear or coming off of the secondary thin coating does not form specks of different colors after a long period of use. If a noble metal is used for the secondary thin coating, the metal material may be a base metal for providing a durable and luxurious coating thereon. If copper or its alloy capable of dry-plating is used for the secondary thin coating, any suitable metal may be plated thereon by a dry- or wet-plating method to form a durable and beautiful metal surfaces.

Further, the secondary thin coating may be provided over the whole surface or in the desired pattern to form a durable and luxurious patterned coating, such as figures or names. As the secondary thin coating 6, any suitable metal or alloy may be selected for providing the durable and beautiful coating.

The coating according to the invention may be provided on a cap crown for a tooth, an outer decoration of a stationery, a band of a wrist watch, an accessory, a container of toiletry, an eye-glass frame, cuffs, a tie-pin, a brooch or other articles.

The essential feature of providing the secondary thin coating by the ion-plating technique in the absence of the inert gas, such as argon or helium, in accordance with the invention may improve operability, workability, economy and quality of the products.

The invention will now be illustrated with a few examples but not limited thereto.

EXAMPLE 1 (Au on TiN)

A degreased and washed SUS 304 plate of 3 cm×3 cm square was placed in an apparatus, and 100 ml/min. of an argon gas was introduced thereinto and a bombard treatment was carried out under a condition of a gas pressure of 0.07 Torr, a voltage of 590 V and a current of 2.2 A for 30 minutes. Then, 90 ml/min. of a nitrogen gas was introduced to provide a gas pressure of $9 \times 10^{-5} - 1.3 \times 10^{-4}$ Torr and a titanium metal was evaporated for 40 minutes under a condition of EB voltage and current of 40 V, 65–75 A and a bias of 350–450 V, 405–5.0 A. Thereafter, the gas was adjusted to $1 \times 10^{-5}$ Torr, and a product was removed after cooling for 40 minutes.

Thus the plate with a TiN coating was obtained.

Figure 4:
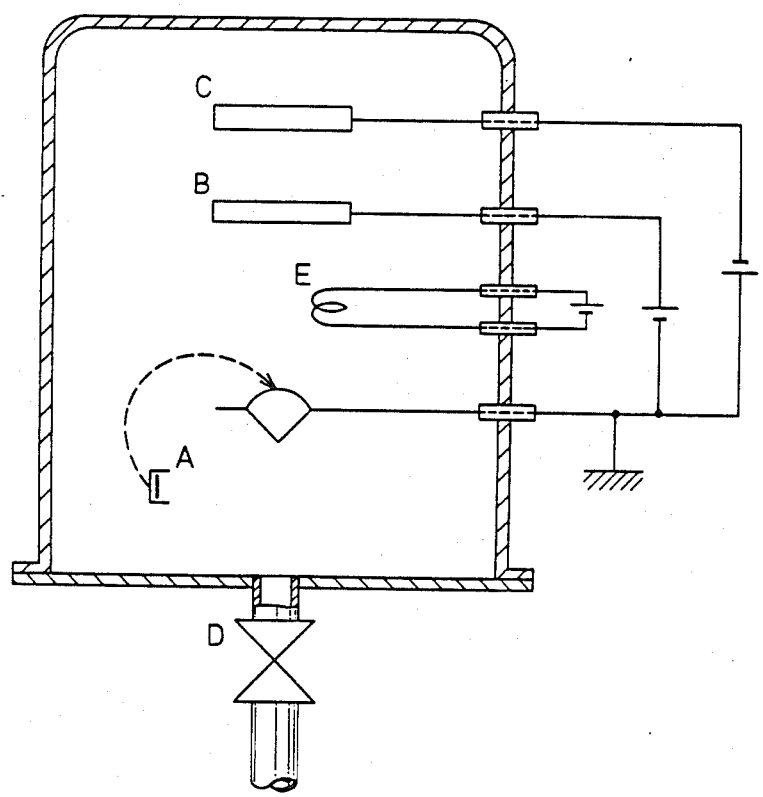
FIG. 4 is a schematic view of an apparatus used for ion-plating the secondary metal film.

Then, the plate with the TiN prime thin coating was placed on a cathode C in an ion-plating apparatus, as shown in FIG. 4, which was evacuated to $10^{-5}$ Torr for allowing Au (gold) to evaporate, using an evaporation source A. The evaporated Au atoms provided a vacuum of approximately $10^{-3} – 10^{-2}$ Torr between the evaporation source A and an anode B arranged adjacent thereto, thereby to generate an arc discharge. In a plasma produced by the arc discharge, the Au atom was ionized according to the following equations:

$$Au \rightleftarrows Au^+ + e^-; \ Au \rightleftarrows Au^{++} + e^{--}$$

The ionized Au ion was accelerated and deposited onto a cathode (substrate) placed outside the anode to form a thin film. The secondary thin Au coating thus formed in the absence of the argon gas had a high adhesive property with respect to the prime TiN coating. In this example the secondary thin coating was ion-plated under the following condition:

Applied Voltage between A* and B* : 40 V
 Applied Voltage between A* and C* : 200 V
 Evaporation Rate : 0.5 g/min.
 Treatment Duration : 5 min.
 (Of course, the inert gas was not present.)

EXAMPLE 2 (Pd on TiN)

After a square SUS 304 plate of 3 cm×3 cm had been ion-plated with a prime TiN thin coating as in Example 1, it was subjected to ion-plating procedure in the same apparatus and the same operation as in Example 1 in the absence of the inert gas to provide a secondary Pd (palladium) thin coating. This secondary thin coating was formed under the following condition:

Applied Voltage between A* and B* : 40 V
 Applied Voltage between A* and C* : 150 V
 Evaporation Rate : 1 g/min.
 Treatment Duration : 3 min.

EXAMPLE 3 (Cr on TiN)

An sample coated with a TiN coating as in Example 1 was placed on the cathode C in the apparatus of FIG. 4 and subjected to the ion-plating procedure in the absence of the inert gas as in Example 1, using Cr (chrome) as an essential element to form a secondary Cr thin coating on the TiN prime coating. In this case, a tungsten thermionic emission electrode was used for generating thermoelectrons between the evaporation source A and the anode B thereby to produce the arc discharge. The secondary thin coating was formed under the following condition:

Applied Voltage between A* and B* : 80 V
 Applied Voltage between A* and C* : 300 V
 Evaporation Rate : 1 g/min.
 Treatment Duration : 10 min.
 Supplied Power to the Thermoelectronic Electrode : 150 W Note
A:Evaporation Source
B:Anode
C:Cathode Although the invention has been described hereinabove with the preferred embodiments, it will be appreciated by those skilled in the art that many variations may be made without departing from the scope and spirit of the invention.

What is claimed is:

1. A method of processing a metal article, comprising the steps of:
 subjecting a metal article having a metal surface to bombardment treatment in the presence of an inert gas;
 ion-plating onto said metal surface a first layer of a metal compound selected from group consisting of chromium nitride, titanium nitride and titanium carbide, said metal compound being ion-plated in the presence of an active gas;
 ion-plating an elemental metal or an alloy of said elemental metal onto said metal material having said first layer, to form a second layer of said elemental metal or said alloy thereof, said elemental metal being ion-plated by an arc discharge in the absence of inert gas.

2. A method according to claim 1, wherein the inert gas is argon and the active gas is nitrogen.

3. A method according to claim 1, wherein the elemental metal is selected from a group consisting of gold, silver, platinum, copper, zinc, palladium, chromium, rhodium, indium, nickel, germanium, cobalt, zirconium, tungsten, tantalum, niobium, manganese, molybdenum, tin, iron, and aluminium.

4. A method according to claim 1, wherein at least one of said first and second layers is deposited on said metal surface in a desired pattern.

* * * * *